US00PP15299P2

(12) United States Plant Patent
Veyna et al.

(10) Patent No.: US PP15,299 P2
(45) Date of Patent: Nov. 9, 2004

(54) FLOWERING PEAR TREE

(50) Latin Name: *Pyrus calleryana×Kawakamii*
Varietal Denomination: Veyna Flowering Pear

(76) Inventors: Sixto C. Veyna, 1619 S. University St., Visalia, CA (US) 93277; Steven C. Veyna, 1619 S. University St., Visalia, CA (US) 93277

( * ) Notice: Subject to any disclaimer, the term of this patent is extended or adjusted under 35 U.S.C. 154(b) by 61 days.

(21) Appl. No.: 10/418,544

(22) Filed: Apr. 17, 2003

(51) Int. Cl.[7] ..... A01H 5/00
(52) U.S. Cl. ..... Plt./177
(58) Field of Search ..... Plt./177

(56) References Cited

U.S. PATENT DOCUMENTS

PP2,489 P 3/1965 Scanlon
PP3,815 P 12/1975 Princeton
PP4,591 P 9/1980 Westwood
PP8,050 P 12/1992 Zampini

*Primary Examiner*—Anne Marie Grunberg

*Assistant Examiner*—S. B. McCormick-Ewoldt

(74) *Attorney, Agent, or Firm*—Mark D. Miller

(57) ABSTRACT

A new and distinct variety of a flowering pear tree named 'Veyna Flowering Pear' which can be readily distinguished from other ornamental flowering pear trees, i.e. 'Bradford' or 'Aristocrat' cultivars of *Pyrus calleryana,* in that this new invention has brighter foliage and larger leaves than the two above-mentioned cultivars, is less pyramidal in form, and produces a brighter and more intense shade of red three weeks later. This new variety is well suited as an attractive ornamental for landscape.

5 Drawing Sheets

BACKGROUND OF THE NEW VARIETY

The present invention refers to a new and distinct variety of flowering pear tree which will hereinafter be denominated as the 'Veyna Flowering Pear', and which produces a bright red foliage during late November to early December in a normal growing year with normal winter chilling temperature in the San Joaquin Valley of Central California. This hybrid flowering pear tree is a vigorous, fast growing ornamental landscape tree which produces larger leaves than either of its parents, with bark color of the mature wood and branches changing from a shade of reddish brown to brown. The young tree less than three year old displays a distinct reddish shade similar to the bark of cherry trees. Trees under stress produce nutlets approximately one half inch in diameter.

ORIGIN AND ASEXUAL REPRODUCTION OF THE NEW VARIETY

The inventor and owner of this new invention planted two trees at his formal residence in Visalia, Calif. in approximately 1980 within fifteen feet of each other. One tree was an unknown cultivar of *Pyrus kawakammii* and the other was the 'Aristocrat' cultivar of *Pyrus calleryana*. Although the blooming period of the two varieties would be different, depending on the degree of winter chilling that occurred, in some rare years the bloom period will overlap and cross pollination of the two occurs. Collection of *Pyrus calleryana* seed had been performed for production of liners (seedlings). In 1987 the seed collected produced seedling of the resulting trees (hybrid). During the next succeeding years the production manager and co-owner of the nursery observed multiple trees in the liner block that exhibited a greater variety of fall color and leaf size and shape than normal. From these variable trees he selected 31 for testing of the nursery bud wood in an orchard near Visalia, Calif. One of these trees was then selected as the mother tree. Buds from this mother tree were grafted onto *Pyrus betulaefolia* rootstock in the dormant season of 1998–1999 (4 trees) and an additional 300 trees were grafted in the dormant season of 2000–2001 in Visalia, Calif. The inventor carefully examined and compared the asexually reproduced trees with the mother tree and in all respects they are identical. The observed tree was three years old.

BRIEF SUMMARY OF THE NEW VARIETY

The flowering pear tree of the present invention is well suited for use as an attractive tree for ornamental landscaping. It can be readily distinguished from other ornamental flowering pear trees such as the 'Bradford' or 'Aristocrat' cultivars of *Pyrus calleryana,* because it has brighter foliage and larger leaves, is less pyramidal in form, and produces a brighter and more intense shade of red three weeks later than either of the two above-mentioned cultivars.

BRIEF DESCRIPTION OF THE DRAWINGS

The included color photographs display the following.

DETAILED BOTANICAL DESCRIPTION

Figure 1:
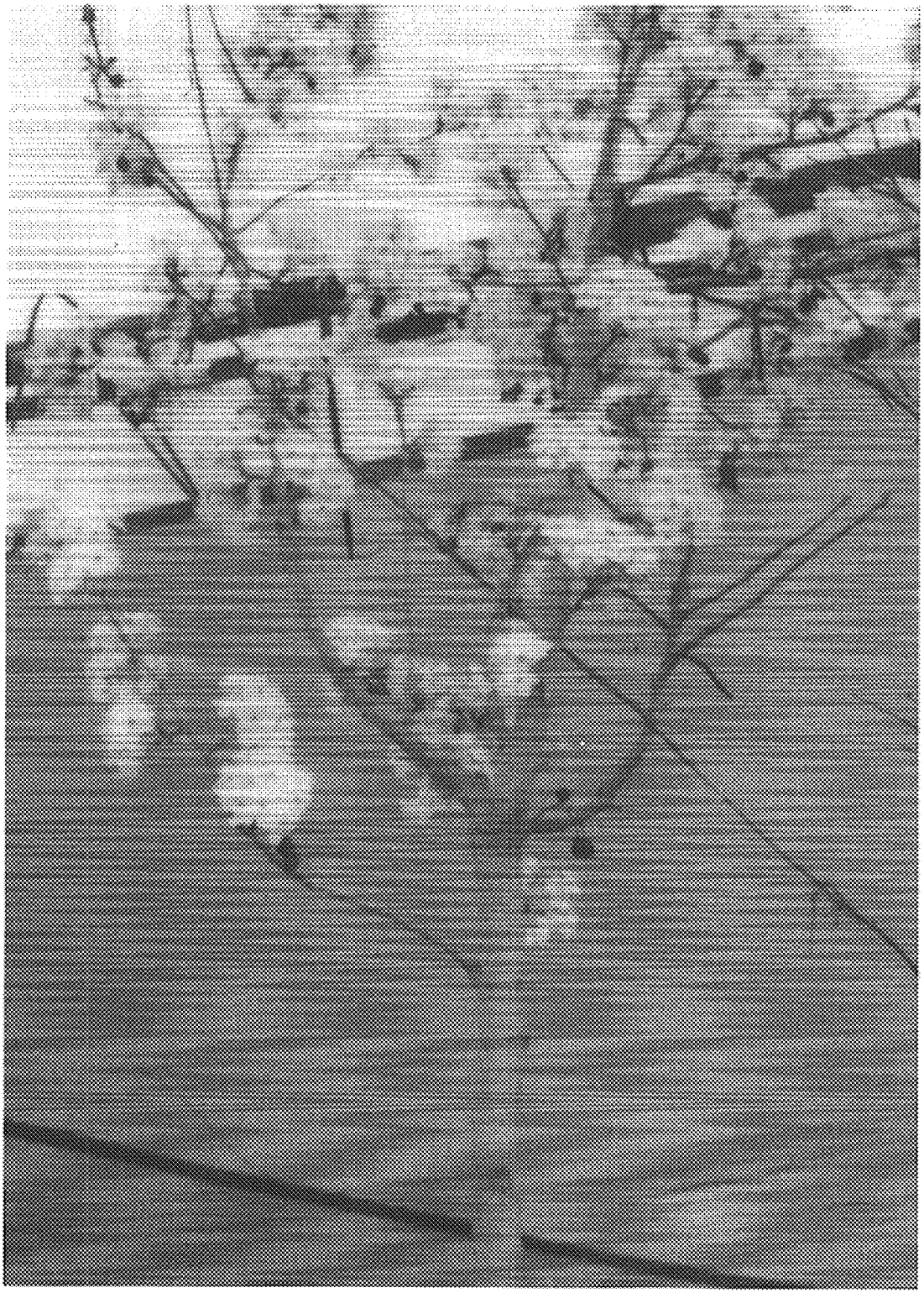
FIG. 1 is a photograph showing the flowering of the third leaf progeny.
Figure 2:
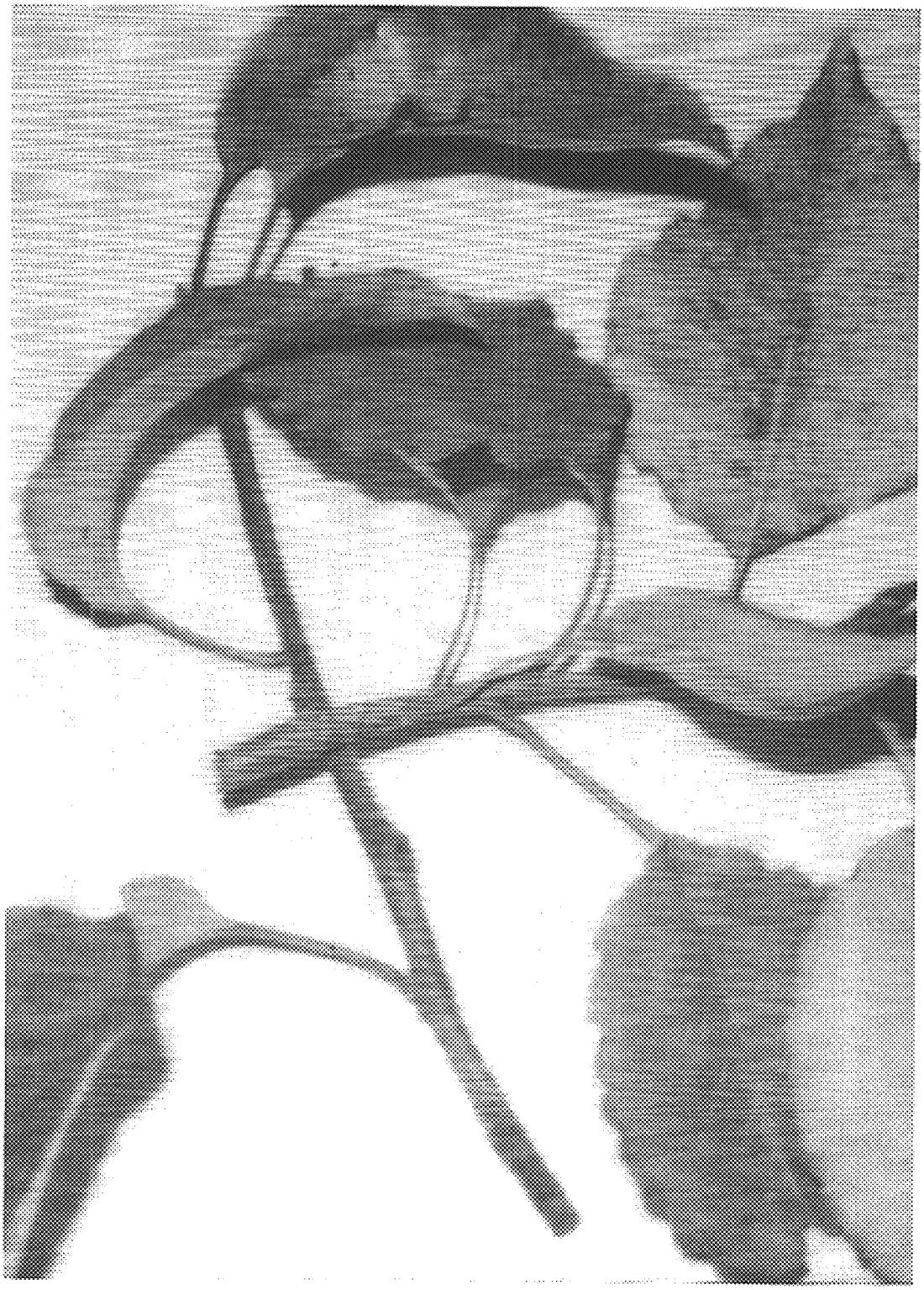
FIG. 2 is a photograph showing the foliage, both upper and lower surface, of the third leaf progeny.
Figure 3:
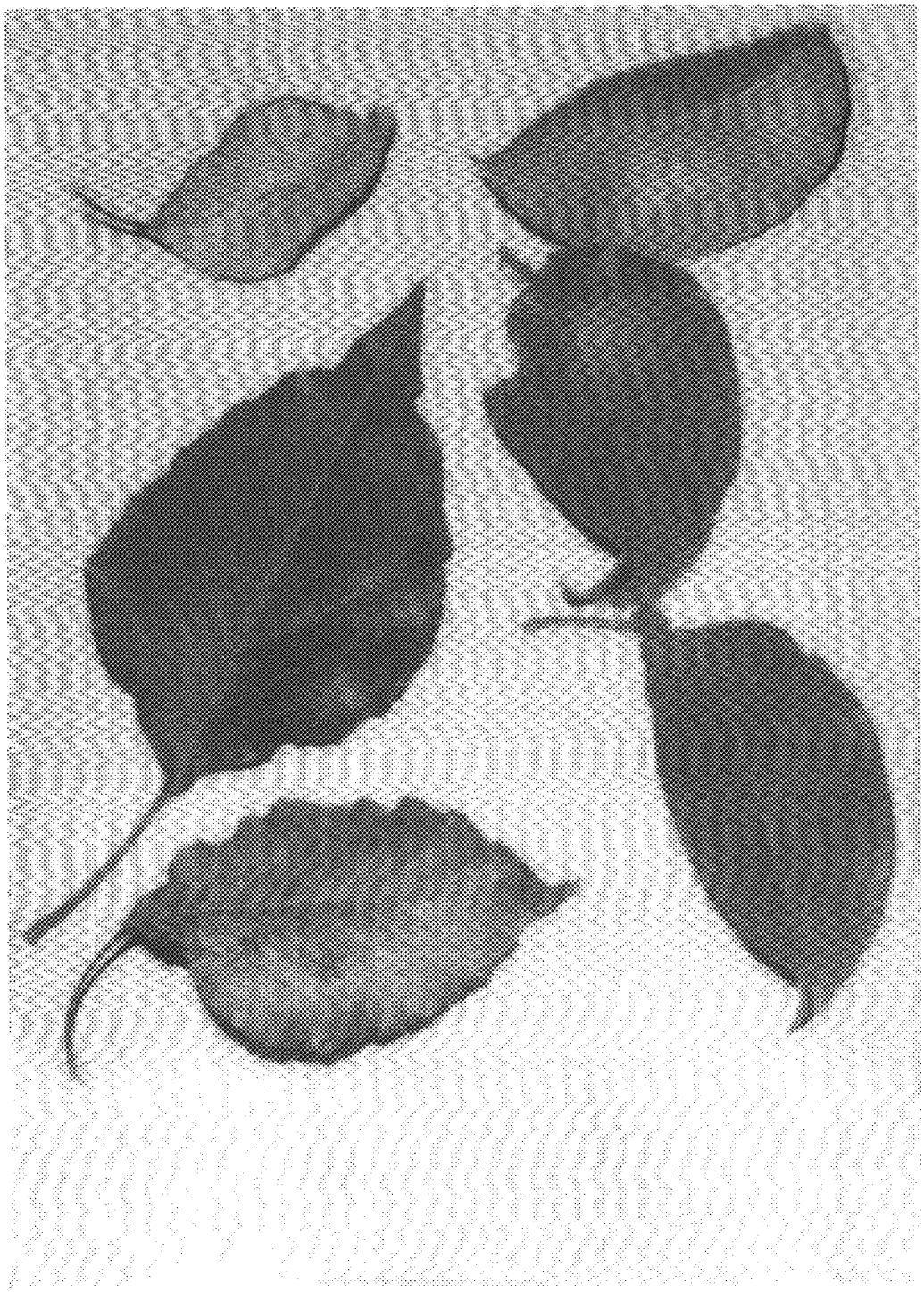
FIG. 3 is a photograph showing the fall foliage alongside normal green foliage color from the third leaf progeny.
Figure 4:
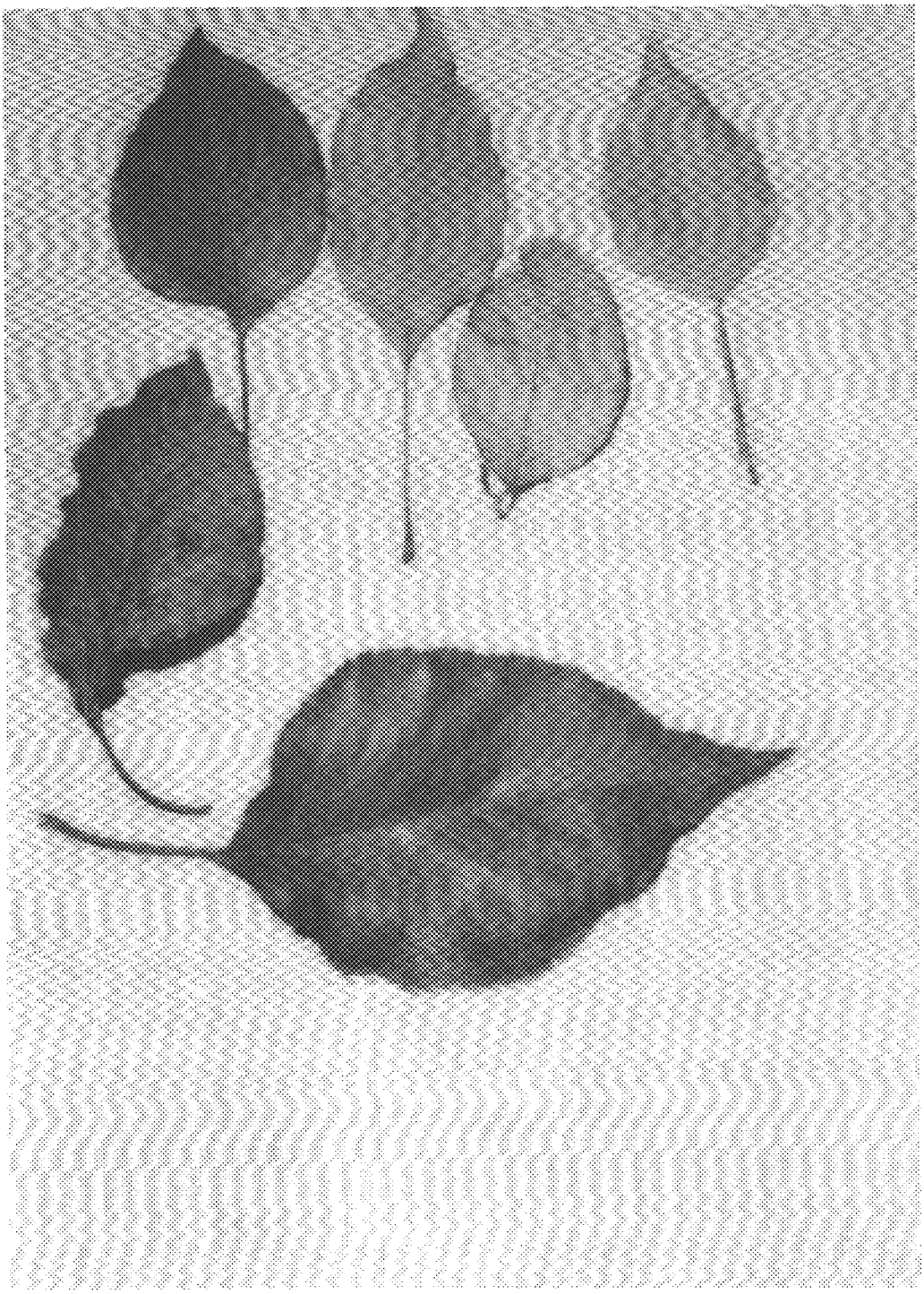
FIG. 4 is a photograph showing a comparison of the leaves, both color and size, of the present invention with 'Bradford' pear. The two leaves along the left margin and the large center leaf are the present invention, and the three remaining leaves along the top row are from the 'Bradford' pear.
Figure 5:
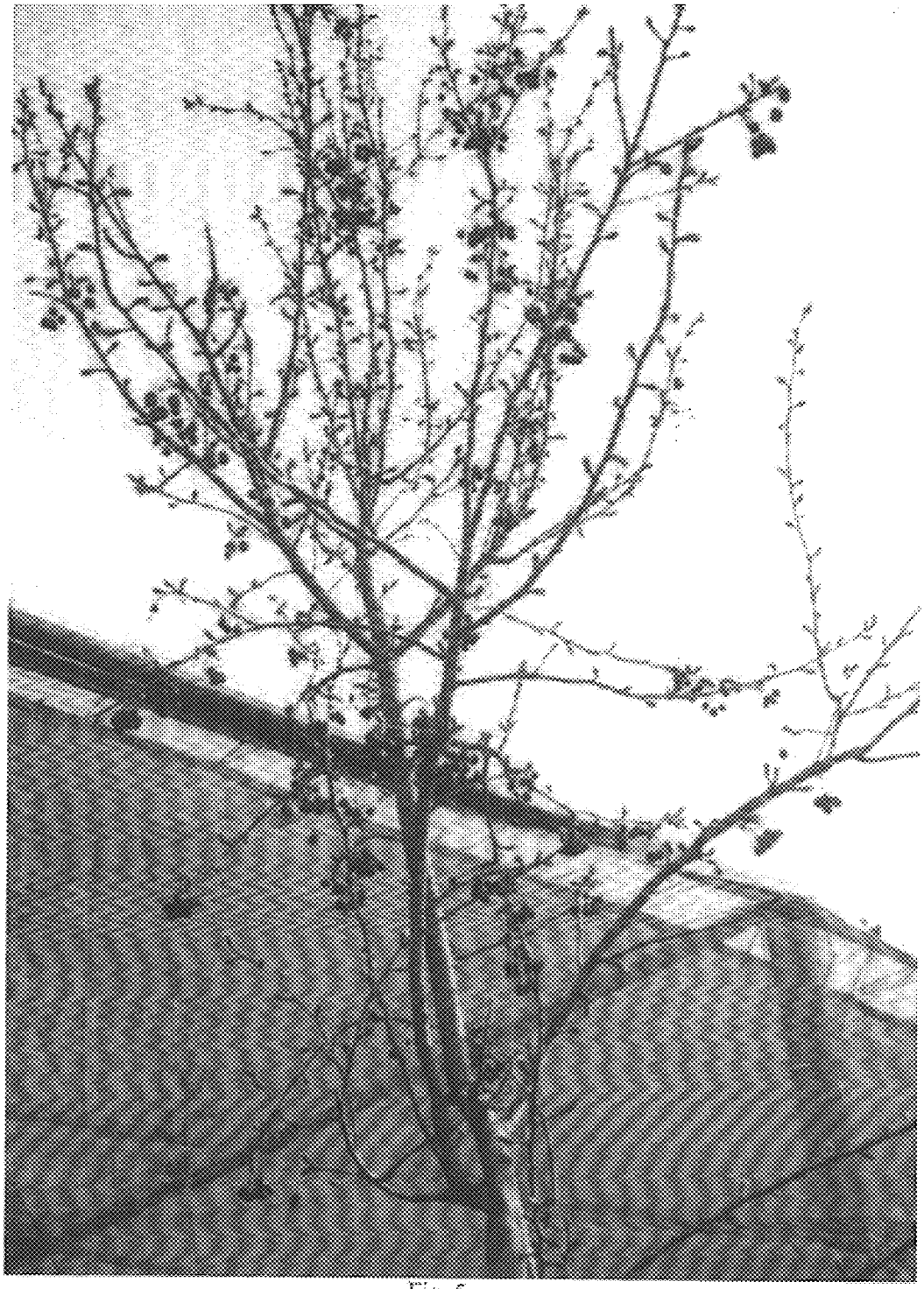
FIG. 5 is a photograph showing a container-borne (stressed) tree of the present invention displaying the branches and nutlets.

Referring more specifically to the pomological description of the new and distinct variety of the flowering pear tree, the following details are provided under the ecological conditions prevailing in the nursery planting of origin which is located near the town of Tulare, Calif. in the San Joaquin Valley of Central California. All major color designations are by reference to the Dictionary of Color by Maerz & Paul, First Edition, 1930. Common color names are occasionally employed.

TREE

Size: This third leaf tree is approximately 12–14 feet high and 3 feet wide.
Vigor: Very good.
Figure: Upright and slightly spreading, not as pyramidal as 'Bradford' pear.
Trunk:
- *Size.*—8–9 inches in circumference 14–16 inches above soil level.
- *Bark.*—Comparatively smooth.
- *Color.*—Canyon (7-E-7).

Lenticels: Moderate in number.
- *Size.*—4–7 mm (0.16–0.28 inch).
- *Color.*—Brown.

Branch size: 3–4 inches in circumference.
- *Angle.*—At branches at crotch of tree is approximately 40°.
- *Surface.*—Smooth for both mature and immature branches.
- *Color.*—Mature branches: Cordovan (8-H-8), Woodland Brown. Immature branches Andorra (8-L-4).

LEAVES

Size: Medium to large.
- *Length.*—90–130 mm (3.54–5.12 inches).
- *Width.*—59–73 mm (2.32–2.87 inches).

Shape: Oval — Acuminate. Upwardly disposed surface, Pomegranate (6-L-6). Downwardly disposed surface, Jonquil (3-J-5r).
Marginal form: Crenate.
Arrangement: Alternate.
Venation pattern: Pinnate.
Texture: Smooth.
Leaf vein:
- *Color.*—Peony R+ (6-J-6).
- *Thickness.*—1 mm (0.04 inch).

Glandular characteristics: None.
Petiole: Medium to large.
- *Length.*—30–42 mm (1.18–1.65 inch).
- *Diameter.*—1 mm (0.04 inch).
- *Color.*—Peony R+ (6-J-6).

FLOWERS

Flower buds: Hardy under San Joaquin Valley climatic conditions.
- *Size.*—Dormant buds in clusters of 10–12. Diameter — 5 mm (0.20 inch). Length: 6–8 mm (0.24–0.32 inch).
- *Form.*—Conic.
- *Color.*—White with a pink tinge (1-B-1).

Flowers: Generally showy.
- *Date of bloom.*—As of the end of February, 75–85% in clusters of 3–10. As of mid March, 100%.

Duration: Approximately 15 days.
Size: Medium.
Diameter when fully expanded: 23–26 mm (0.91–1.02 inch).
Bloom quantity: Abundant.
Fragrance: Mild.
Petals: 5.
- *Size.*—Small to medium.
- *Length.*—8–12 mm (0.32–0.47 inch).
- *Width.*—8–12 mm (0.32–0.47 inch).
- *Form.*—Broadly ovate.
- *Petal margins.*—Undulated with apex slightly rounded.
- *Color.*—Upper surface, white (1-A-1); lower surface, white (1-A-1).

Flower pedicel:
- *Size.*—Moderate in length, 22–28 mm (0.87–1.1 inch).
- *Color.*—Viridine Y (17-L-7).

Sepals: 5.
- *Color.*—Chrome Green (23-H-12).
- *Surface.*—Slightly pubescent.
- *Size.*—Medium.
- *Form.*—Broadly ovate.

Calyx:
- *Size.*—3–5 mm (0.12–0.20 inch).
- *Color.*—Akbar+ (7-L-4).

Anthers:
- *Size.*—Small.
- *Color.*—Viridine Green (17-I-6).

Stamens:
- *Number of stamens.*—20.
- *Size.*—5–7 mm (0.20–0.28 inch) long.
- *Filament.*—White.

Pistil:
- *Length.*—7–8 mm (0.28–0.32 inch).
- *Color.*—Light Green (17-L-5).
- *Surface.*—Slightly pubescent.

OTHER INFORMATION

The invention appears to be resistant to fire blight. No seeds are produced. As a flowering pear with perfect flowers, no pollination is required.

We claim:

1. A new and distinct variety of a flowering pear tree named 'Veyna Flowering Pear' substantially as illustrated and described that is well suited as an attractive ornamental for landscape, and which can be readily distinguished from other ornamental flowering pear trees, such as the 'Bradford' or 'Aristocrat' cultivars of *Pyrus calleryana,* in that this new invention has brighter foliage and larger leaves, is less pyramidal in form, and produces a brighter and more intense shade of red leaves three weeks later than either of the two mentioned cultivars.

* * * * *